(12) United States Patent
Ang

(10) Patent No.: US 12,171,531 B2
(45) Date of Patent: *Dec. 24, 2024

(54) HEMODYNAMIC ANALYSIS SYSTEM

(71) Applicant: The Regents of the University of California, Oakland, CA (US)

(72) Inventor: Lawrence Ang, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/450,308

(22) Filed: Aug. 15, 2023

(65) Prior Publication Data

US 2024/0148261 A1 May 9, 2024

Related U.S. Application Data

(63) Continuation of application No. 16/887,080, filed on May 29, 2020, now Pat. No. 11,766,184.

(Continued)

(51) Int. Cl.
*A61B 5/0215* (2006.01)
*A61B 5/00* (2006.01)
(Continued)

(52) U.S. Cl.
CPC ...... *A61B 5/02158* (2013.01); *A61B 5/02108* (2013.01); *A61B 5/026* (2013.01);
(Continued)

(58) Field of Classification Search
CPC . A61B 5/02158; A61B 5/02108; A61B 5/026; A61B 5/7278; A61B 5/746; A61B 5/6852; A61B 5/6862; A61M 2025/0166
See application file for complete search history.

(56) References Cited

U.S. PATENT DOCUMENTS

| | | | |
|---|---|---|---|
| 11,766,184 B2 * | 9/2023 | Ang | A61B 5/7278 600/486 |
| 2008/0269572 A1 * | 10/2008 | Kanz | A61B 5/0006 600/301 |
| 2016/0296288 A1 * | 10/2016 | Sankaran | A61B 6/5217 |

OTHER PUBLICATIONS

Oi et al., "Utility of nicorandil for the measurement of coronary fractional flow reserve" published on Sep. 2013 (Year: 2013).*

(Continued)

*Primary Examiner* — Keith M Raymond
*Assistant Examiner* — Fikirte (Fiki) T Ashine
(74) *Attorney, Agent, or Firm* — Mintz Levin Cohn Ferris Glovsky and Popeo, P.C.

(57) ABSTRACT

Articles of manufacture, including an apparatus for detecting a hemodynamic disorder, are provided. A method may include receiving a blood pressure, including an aortic pressure and a distal coronary pressure, over a plurality of heartbeats. The method also includes determining a complement of a ratio of the distal coronary pressure to the aortic pressure for each heartbeat of the plurality of heartbeats. The method also includes determining, based on the complement of the ratio, a maximum complement of the ratio and a minimum complement of the ratio. The method also includes determining, based on the maximum complement and the minimum complement, a pressure-derived coronary flow reserve. The pressure-derived coronary flow reserve includes a ratio of the maximum complement to the minimum complement. The method also includes detecting, based on the pressure-derived coronary flow reserve, a hemodynamic disorder.

17 Claims, 12 Drawing Sheets

Related U.S. Application Data

(60) Provisional application No. 62/855,786, filed on May 31, 2019.

(51) Int. Cl.
    *A61B 5/021*     (2006.01)
    *A61B 5/026*     (2006.01)
    *A61M 25/01*     (2006.01)

(52) U.S. Cl.
    CPC ............ *A61B 5/7278* (2013.01); *A61B 5/746* (2013.01); *A61B 5/6852* (2013.01); *A61B 5/6862* (2013.01); *A61M 2025/0166* (2013.01)

(56) References Cited

OTHER PUBLICATIONS

Akasaka, T., et al. "Assessment of coronary flowreserve by coronary pressure measurement: Comparison with flow-or Velocity-Derived coronary flow reserve." Journal of the American College of Cardiology 41.9 (2003): 1554-1560.

Davies, J.E., et al. "Use of the instantaneous wave-free ratio or fractional flow reserve in PCI." New England Journal of Medicine 376.19 (2017): 1824-1834.

De Bruyne, B., et al. "Fractional flow reserve-guided PCI for stable coronary artery disease." The New England Journal of Medicine 371.13 (2014): 1208-1217.

Joye, J. D., et al. "Intracoronary Doppler guide wire versus stress single-photon emission computed tomographic thallium-201 imaging in Assessment of Intermediate coronary Stenoses" J Am Coll Cardiol 1994;24:940-7.

MacCarthy, P., et al. "Pressure-derived measurement of coronary flow reserve." Journal of the American College of Cardiology 45.2 (2005): 216-220.

Patel, M.R et al., "ACC/AATS/AHA/ASE/ASNC/SCAI/SCCT/STS 2017 Appropriate Use Criteria for Coronary Revascularization in Patients With Stable Ischemic Heart Disease: A Report of the American College of Cardiology Appropriate Use Criteria Task Force, American Association for Thoracic Surgery, American Heart Association, American Society of Echocardiography, American Society of Nuclear Cardiology, Society for Cardiovascular Angiography and Interventions, Society of Cardiovascular Computed Tomography, and Society of Thoracic Surgeons," Journal of the American College of Cardiology 69.17 (2017): 2212-2241.

Shalman, E., et al. "Pressure-based simultaneous CFR and FFR measurements: understanding the physiology of a stenosed vessel." Computers in Biology and Medicine 31.5 (2001): 353-363.

Tonino, P.A.L., et al. "Fractional Flow Reserve versus Angiography for Guiding Percutaneous Coronary Intervention." N Engl J Med 360 (2009): 213-24.

van de Hoef, T.P., et al. "Physiological basis and long-term clinical outcome of discordance between fractional flow reserve and coronary flow velocity reserve in coronary stenoses of intermediate severity." Circulation: Cardiovascular Interventions 7.3 (2014): 301-311.

Wijntjens, G.W.M., et al. "Pressure-derived estimations of coronary flow reserve are inferior to flow-derived coronary flow reserve as diagnostic and risk stratification tools." International Journal of Cardiology 279 (2019): 6-11.

\* cited by examiner

HEMODYNAMIC ANALYSIS SYSTEM

CROSS-REFERENCE TO RELATED APPLICATIONS

This application is a continuation of U.S. patent application Ser. No. 16/887,880 filed May 29, 2020, now U.S. Pat. No. 11,766,184, entitled "HEMODYNAMIC ANALYSIS SYSTEM," which claims benefit of priority to U.S. Provisional Application No. 62/855,786, filed on May 31, 2019, entitled "TOOL FOR HEMODYNAMIC ANALYSIS," the disclosures of which are incorporated herein by reference in their entirety.

FIELD

The subject matter described herein relates generally to a hemodynamic analysis system and more specifically to a pressure-derived coronary flow reserve-based hemodynamic analysis system for detecting a hemodynamic disorder.

BACKGROUND

Several techniques are available in a clinical setting to provide measurements of coronary blood flow, including techniques based on a fractional flow reserve ("FFR") and a coronary flow reserve ("CFR"). These measurements may be used to evaluate the coronary blood flow and to detect various hemodynamic disorders, such as a blood flow restriction and/or coronary artery disease. For example, CFR-based techniques may be used to evaluate microvascular function and involve comparing a change in blood flow velocity and/or a change in temperature at a single location along a blood flow path. On the other hand, FFR-based techniques may be used to evaluate the degree of flow-limiting disease within large epicardial coronary arteries and involve measuring a change in pressure at two locations along the blood flow path.

SUMMARY

Articles of manufacture, including apparatuses, and methods for hemodynamic analysis based on a pressure-derived coronary flow reserve are provided.

According to some aspects, a method may include receiving, from one or more sensors positioned within a cardiovascular structure of a patient, a blood pressure over a plurality of heartbeats. The blood pressure may include an aortic pressure and a distal coronary pressure. The method may include determining a complement of a ratio of the distal coronary pressure to the aortic pressure for each heartbeat of the plurality of heartbeats. The method may also include detecting, based on the complement of the ratio of the distal coronary pressure to the aortic pressure, a hemodynamic disorder within the cardiovascular structure of the patient.

In some aspects, the method may also include determining, based on the complement of the ratio, a maximum complement of the ratio and a minimum complement of the ratio. The method may also include determining, based on the maximum complement and the minimum complement, a pressure-derived coronary flow reserve. The pressure-derived coronary flow reserve may include a ratio of the maximum complement to the minimum complement.

In some aspects, the detecting is further based on the pressure-derived coronary flow reserve.

In some aspects, the determining the complement of the ratio further includes aggregating the complement of the ratio of the plurality of heartbeats. The determining the complement of the ratio may also include determining, based on the aggregated complement of the ratio, the maximum complement and the minimum complement.

In some aspects, the detecting further includes comparing the pressure-derived coronary flow reserve to a threshold. The detecting may also include detecting the hemodynamic disorder when the pressure-derived coronary flow reserve is less than or equal to the threshold.

In some aspects, the one or more sensors includes a first sensor coupled to a first insertion tool and a second sensor coupled to a second insertion tool. The first sensor may measure the aortic pressure and the second sensor may measure the distal coronary pressure.

In some aspects, the method also includes equalizing the aortic pressure and the distal coronary pressure when the first sensor and the second sensor are positioned at the same location.

In some aspects, the receiving further includes: receiving the aortic pressure from the first sensor and the distal coronary pressure from the second sensor when the second sensor is positioned downstream of an anatomical restriction.

In some aspects, the receiving further includes receiving the aortic pressure and the distal coronary pressure after a medication has been introduced to the cardiovascular structure. The medication may cause the cardiovascular structure to dilate.

In some aspects, the cardiovascular structure comprises one or more of an artery and a vessel.

In some aspects, the method also includes generating, based on the detection of the hemodynamic disorder, an alert indicating that the pressure-derived coronary flow reserve is less than or equal to a threshold.

Implementations of the current subject matter can include methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a non-transitory computer-readable or machine-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including, for example, to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a rechargeable battery, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings, FIG. 1 schematically depicts a hemodynamic analysis system, consistent with implementations of the current subject matter.

When practical, similar reference numbers denote similar structures, features, and/or elements.

DETAILED DESCRIPTION

Figure 1:
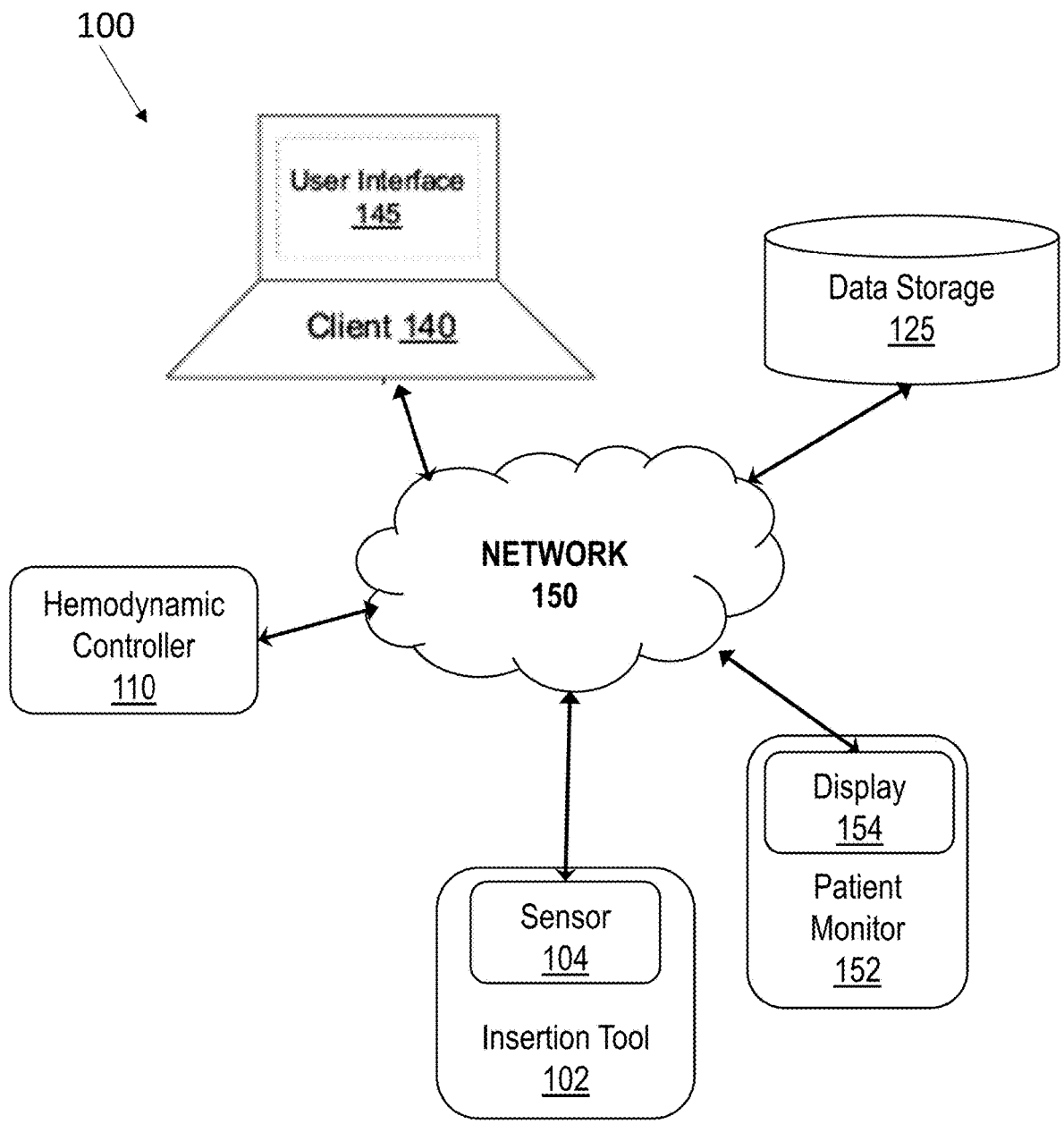

Several techniques may be available in a clinical setting to provide measurements of coronary blood flow, including fractional flow reserve ("FFR") and coronary flow reserve ("CFR"). These measurements may be used to evaluate the coronary blood flow and to detect various hemodynamic disorders. However, these techniques may produce inaccurate and inconsistent results, and may thus be impractical in use. The hemodynamic analysis system described herein provides more accurate and consistent measurements, leading to better and more efficient detection of hemodynamic disorders, such as such as a blood flow restriction, Coronary Artery Disease ("CAD"), and/or other diseases of the heart muscle, valves or coronary arteries. For example, the hemodynamic analysis system may receive real-time patient telemetry data and determine, based on the data, unique measurements, such as a non-diastolic, diastolic, and/or whole-cardiac cycle pressure-derived CFR (also referred to herein as "CFRp"), that provides more useful information, and more accurately, quickly, consistently, and/or efficiently detects hemodynamic disorders.

CFR may be used to evaluate microvascular function and indicates the ability of the coronary artery microvasculature to maximally dilate and increase coronary artery flow, but is not used to quantify epicardial vessel disease. An abnormal CFR identifies diseased microvasculature warranting medical therapy and/or compensatory dilation in the presence of an upstream obstruction. Generally, CFR is calculated by comparing an amount of blood flow the arteries in the heart can produce at a single source location during two different coronary flow states.

In particular, CFR may be calculated using two methods. In one method, an ultrasound Doppler is used to compare changes in blood velocity, such as by comparing hyperemic blood velocities to a baseline blood velocity at a single location. However, Doppler-based wires are relatively unwieldy and challenging to manipulate within the coronary anatomy, making them impractical for routine hemodynamic studies, during Percutaneous Coronary Intervention (PCI), and for detecting hemodynamic disorders. Doppler-based CFR systems may additionally and/or alternatively be inaccurate, and/or provide poor reproducibility. For example, Doppler signals at any point of the cardiac cycle may be overestimated due to signal noise and artifacts, or underestimated due to suboptimal wire angulation away from the direction of flow and/or positioning against the blood vessel wall. Also, optimal signals acquired at baseline flow may deteriorate during hyperemia. Any of these suboptimal Doppler measurements introduces CFR calculation errors, and thus leads to improperly diagnosed hemodynamic disorders. The hemodynamic analysis system described herein provides more accurate and consistent measurements, leading to better and more efficient detection of hemodynamic disorders.

Another method for calculating CFR includes a comparison of thermodilutional flow rates. In this method, a cold saline or other solution is injected through a wire positioned at least partially within the patient. To determine the CFR using this method, a thermodilution curve is created over multiple heart beats and used to derive coronary blood flow. However, thermodilutional CFR measurements may be poorly reproducible, user-dependent, and time-consuming. This technique also requires intravenous adenosine infusion, rather than an intracoronary adenosine bolus, to induce continuous hyperemia for minutes at a time, which prolongs diagnostic procedures. Thus, these systems are also impractical for routine hemodynamic studies, during Percutaneous Coronary Intervention (PCI), and for detecting hemodynamic disorders. Unlike thermodilutional CFR techniques, the hemodynamic analysis system described herein provides more accurate and consistent measurements, leading to better and more efficient detection of hemodynamic disorders.

As noted above, another technique for detecting hemodynamic disorders includes determining an FFR value. FFR-based techniques may be used to evaluate the degree of flow-limiting disease within large (epicardial) coronary arteries, but not to evaluate the condition of distal microscopic blood vessels (e.g., microvasculature). FFR-based techniques generally involve measuring a change in pressure at two locations along the blood flow path. For example, FFR is a measurement derived from comparing simultaneous invasive blood pressure measurements acquired proximal to (e.g., upstream) and distal to (e.g., downstream) a segment of diseased coronary artery, and obtained during maximal coronary blood flow (hyperemia). This technique may help to detect CAD, which causes resistance to blood flow, thus increasing distal vessel blood velocity, decreasing distal vessel blood pressure, and increasing the difference between proximal and distal pressure measurements.

FFR is calculated as the ratio of distal pressure ("Pd") to proximal aortic pressure ("Pa") during hyperemia, and represents the proportion of blood flow achieved in the presence of the interrogated coronary artery obstruction compared to blood flow achieved without obstruction. Thus, FFR values of 1.0 indicate unobstructed blood flow through an interrogated vessel segment. FFR-based techniques include analyzing an instantaneous wave-free ratio (iFR) that reports resting Pd/Pa ratio specifically during relaxation of the ventricular heart chamber (diastole) when coronary blood flow predominantly occurs. Additionally and/or alternatively, FFR-based techniques include analyzing an average resting Pd/Pa measured indiscriminately across the entire cardiac cycle. Both measurements are recorded without inducing hyperemia. However, FFR-based techniques may be inconsistent and are limited to detecting pressure changes in only a small section of an artery, rather than throughout the vascular structure. Thus, FFR-based techniques may be unable to detect hemodynamic disorders that impact an overall cardiovascular structure, and/or that occur in multiple locations throughout the cardiovascular structure. Unlike FFR-based techniques, the hemodynamic analysis system described herein provides more accurate and consistent measurements, leading to better and more efficient detection of hemodynamic disorders.

CFR-based techniques and FFR-based techniques may also be independent of one another and are derived using different procedures. For example, as noted above, CFR-based techniques may be used to evaluate microvasculature, while FFR-based techniques may be used to evaluation larger arteries. Also, patients with discordant CFR and FFR measurements, particularly with abnormal CFR<2.0 and normal FFR>0.80, possess greater risk of adverse cardiac events, further emphasizing the independence of CFR and FFR in measuring different hemodynamic disorders, such as various CAD conditions. The hemodynamic analysis system described herein may be desirably used to evaluate an overall cardiovascular structure, providing a broader indication of the patient's overall cardiovascular health.

FIG. 1 depicts a system diagram illustrating hemodynamic analysis system 100, in accordance with some example implementations. Referring to FIG. 1, the hemodynamic analysis system 100 may include an insertion tool 102, a sensor 104, a client 140 including a user interface 145, a patient monitor 152 including a display 154, a data storage 125, and a hemodynamic controller 110.

The insertion tool 102, the sensor 104, the client 140, the patient monitor 152, the display 154, the data storage 125, and/or the hemodynamic controller 110 may be communicatively coupled via a network 150 and/or Bluetooth. The network 150 may be any wired and/or wireless network including, for example, a public land mobile network (PLMN), a wide area network (WAN), a local area network (LAN), a virtual local area network (VLAN), the Internet, and/or the like.

The insertion tool 102 may include a tube (e.g., a long thin tube), a catheter, a stent, a microcatheter, and/or other device configured to be at least partially inserted into the patient's body. The insertion tool 102 may include an interior channel through which one or more medications, dyes, instruments, and/or the like may be inserted into the patient's body (e.g., into the patient's bloodstream). For example, the insertion tool 102 may be used during cardiac catheterization to detect and/or treat certain cardiovascular conditions, such as hemodynamic disorders. In use, the insertion tool 102 may be inserted in an artery or vein in the patient's neck, groin, arm, and/or another location, and threaded through the blood vessels to and/or towards the heart.

The sensor 104 may measure one or more parameters indicating cardiac output, such as a blood pressure (an arterial pressure, a distal coronary pressure, and/or the like), a blood temperature, a blood velocity, and/or the like. For example, the sensor 104 may include a manometer, a pressure sensor, a temperature sensor, a pulse sensor, a velocity sensor, a blood flow sensor, and/or the like. The sensor 104 may be coupled to the insertion tool 102. For example, the sensor 104 may be coupled to a distal tip and/or a proximal tip of the insertion tool 102. In some implementations, the sensor 104 may be coupled to another portion of the insertion tool 102, such as along a length of the insertion tool 102. In some implementations, the sensor 104 includes one, two, three, four, five, six, seven, or eight or more sensors 104. The sensors 104 may be positioned at various positions along a length of the insertion tool 102. For example, the sensors 104 may be positioned at opposite ends of the insertion tool 102, and/or may be spaced apart along the length of the insertion tool 102. The sensors 104 may be communicatively coupled to the patient monitor 152 and/or the display 154.

The display 154 may form a part of the patient monitor 152 or may be separately coupled to the patient monitor 152. The display 154 may also include a user interface. The user interface may form a part of a display screen of the display 154 that presents information to the user and/or the user interface may be separate from the display screen. For example, the user interface may be one or more buttons, or portions of the display screen that is configured to receive an entry from the user.

The client 140 may be a mobile device such as, for example, a smartphone, a tablet computer, a wearable apparatus, and/or the like. However, it should be appreciated that the client 140 may be any processor-based device including, for example, a desktop computer, a laptop computer, a workstation, and/or the like. For example, via the client 140 and/or the patient monitor 152, the user may be able to configure certain parameters of the insertion tool 102 and/or the sensor 104, such as a sampling rate, a measurement interval, and the like. Additionally, in some examples, via the client 140 and/or the patient monitor 152, the user may configure various treatment and/or monitoring protocols.

The data storage 125 may include databases and/or data tables, providing physical data storage within a dedicated facility and/or being locally stored on the patient monitor 152 and/or client 140. Additionally and/or alternatively, the data storage 125 may include cloud-based systems providing remote storage of data in, for example, a multi-tenant computing environment and/or the like. The data storage 125 may also include non-transitory computer readable media.

The hemodynamic controller 110 may be coupled to or otherwise form a part of the insertion tool 102, the sensor 104, the client 140, the patient monitor 152, and/or the display 154. In some implementations, the hemodynamic controller 110 may cause the hemodynamic analysis system 100 to record one or more measurements, and/or detect a hemodynamic disorder. In such instances, the hemodynamic controller 110 may trigger an alert, which may include a notification provided via a user interface 145 at the client 140 and/or the display 154. For example, the notification may be provided via a short messaging service (SMS) text, an email, a webpage, an application, and/or the like. In some implementations, the client 140 may be coupled to or otherwise form a part of the patient monitor 152, the display 154, and/or the like. The data (e.g., the captured measurements) received at the hemodynamic controller 110 may be evaluated by the hemodynamic controller 110 in real time and/or stored at the data storage 125 coupled with the hemodynamic controller 110 for evaluation at a later time.

Figure 2:
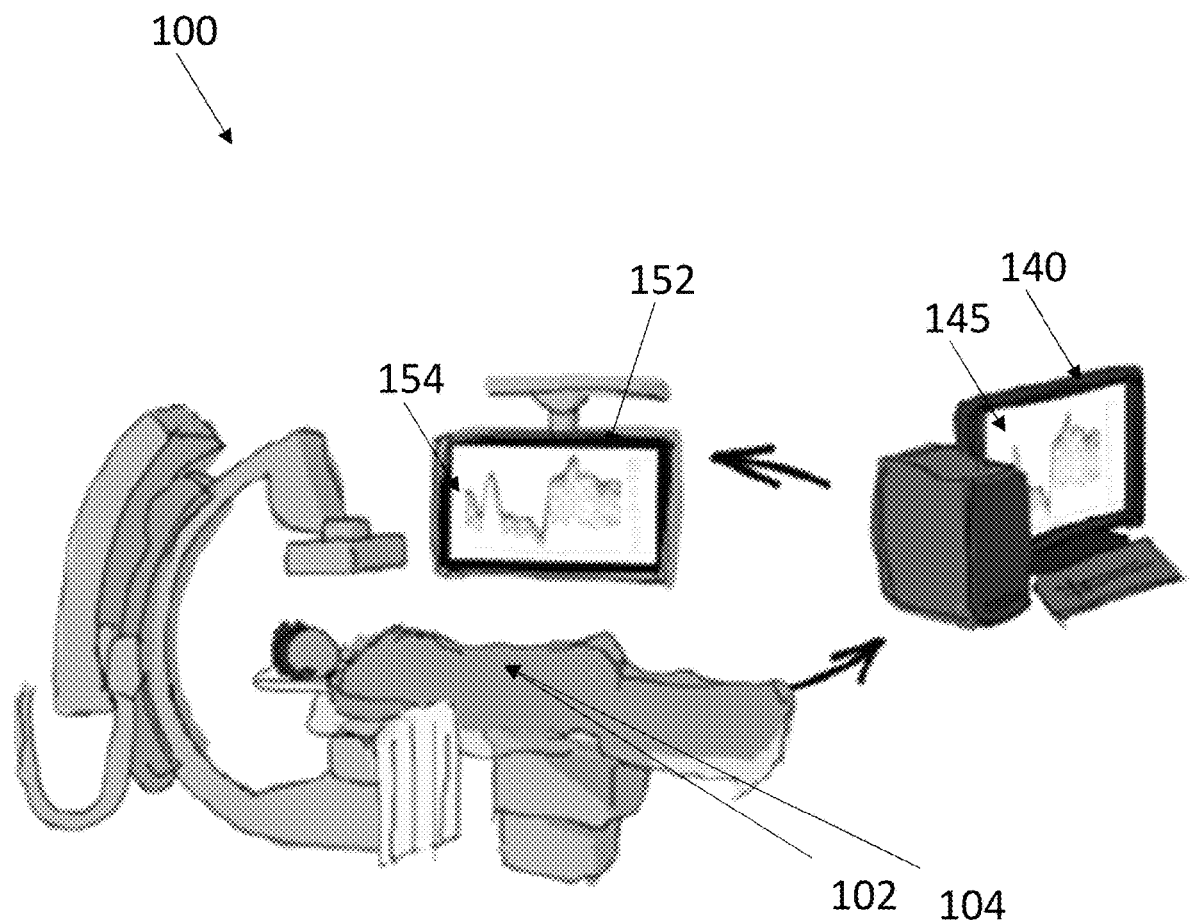
FIG. 2 schematically depicts an example of a hemodynamic analysis system, consistent with implementations of the current subject matter.

FIG. 2 schematically depicts an example of the hemodynamic analysis system 100, consistent with implementations of the current subject matter. Referring to FIG. 2, the hemodynamic analysis system 100 may include the insertion tool 102 and sensor 104, the client 140 including the user interface 145, and the patient monitor 152 including the display 154. As noted above, the sensor 104 may measure one or more parameters indicating cardiac output, such as a blood pressure, including an aortic pressure ("Pa") and a distal coronary pressure ("Pd"), a blood temperature, a blood velocity, and/or the like. The sensor 104 may measure these parameters continuously, at various time intervals (e.g., every millisecond, every 2 milliseconds, every 3 milliseconds, every 4 milliseconds, every 5 milliseconds, every 10 milliseconds, every second, every 5 seconds, every minute, every 30 minutes, every hour and/or the like), and/or at various sampling rates per heart beat (e.g., 1 to 10 samples per beat, 10 to 50 samples per beat, 50 to 100 samples per beat, 100 to 150 samples per beat, 150 to 200 samples per beat, and/or the like). The rate at which the parameters are recorded may be determined via the hemodynamic controller 110 and/or by receipt of an instruction via the user interface 145 of the client 140 and/or the patient monitor 152.

The measured parameters may be transmitted to the client 140 and/or the patient monitor 152 in real-time (e.g., as each measurement is recorded by the sensor 104), at set time intervals, and/or after a scan is completed. In other words, the client 140 and/or the patient monitor 152 may receive the recorded parameters from the sensor 104. Additionally and/or alternatively, the patient monitor 152 may receive the recorded parameters from the client 140 (or vice versa). In some implementations, the hemodynamic controller 110, coupled to and/or forming a part of the patient monitor 152 and/or the client 140, may determine, based on one or more of the recorded parameters, the CFRp. The resulting output may be displayed via the display 154 as a numerical and/or graphical representation.

Consistent with implementations of the current subject matter, the hemodynamic analysis system 100 provides more accurate and consistent measurements, leading to better and more efficient detection of hemodynamic disorders, such as such as a blood flow restriction, Coronary Artery Disease ("CAD"), and/or other diseases of the heart muscle, valves or coronary arteries. For example, the hemodynamic analysis system may receive real-time patient telemetry data and determine, based on the data, unique measurements, such as CFRp, that provides more useful information, and more accurately, consistently, and/or efficiently detects hemodynamic disorders. As discussed in more detail herein, the hemodynamic analysis system 100 (e.g., via the hemodynamic controller 110), matches a baseline of diastolic and/or whole-cardiac cycle Pa and Pd measurements from the same pressure source (e.g., at the same sampling location), measures and/or determines beat-by-beat diastolic and/or whole-cardiac cycle 1-Pd/Pa when inducing hyperemia, measures and/or determines diastolic and/or whole-cardiac cycle 1-Pd/Pa at coronary flow baseline, and/or determines the CFRp, based on the recorded measurements.

Figure 3A:
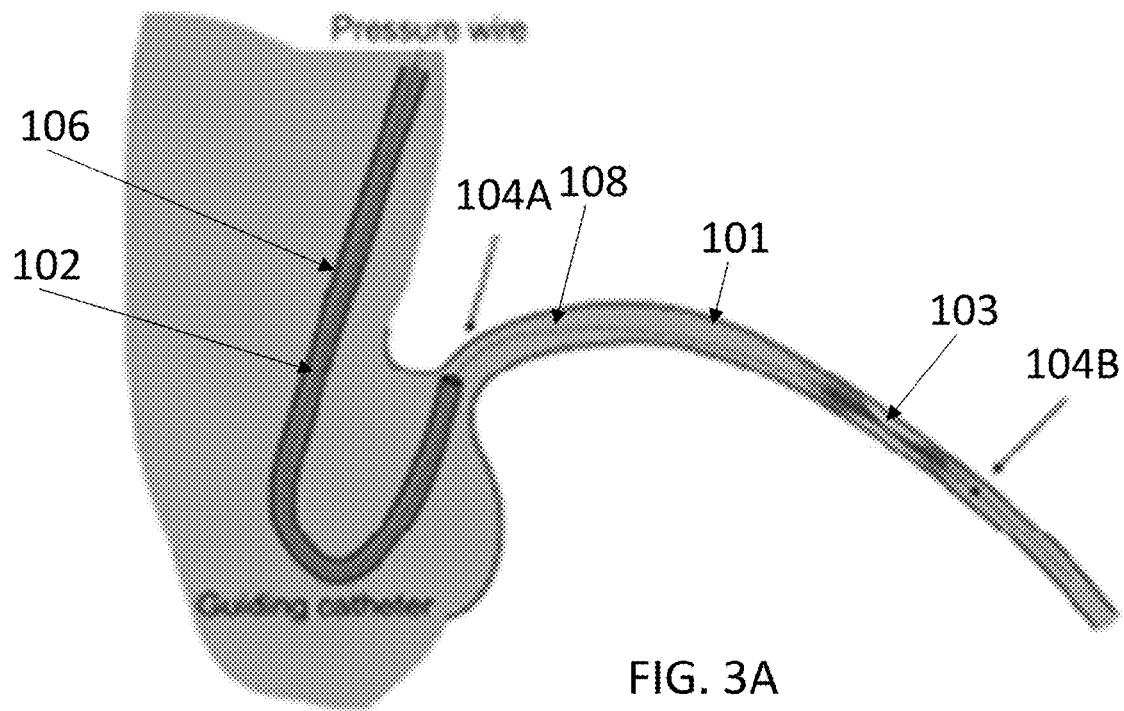
FIG. 3A depicts an example system for collection of hemodynamic measurements, consistent with implementations of the current subject matter.

FIG. 3A illustrates an example of the hemodynamic analysis system 100 in use, consistent with implementations of the current subject matter. For example, as shown in FIG. 3A, the insertion tool 102 may include a first insertion tool, such as a catheter 106 (e.g., a fluid-filled guiding catheter) and a second insertion tool, such as a pressure wire 108 extending through and beyond the first insertion tool 106 along a blood flow path in an artery. Though certain examples described herein include a catheter and a pressure wire, other implementations are consistent with the current subject matter, such as a first insertion tool and the second insertion tool being the same instruments (such that the one or more sensors 104 are positioned on the same instrument), and/or the first insertion tool and the second insertion tool being different instruments, such as a catheter, microcatheter, pressure wire, tube, or other instrument on which the one or more sensors are positioned. The insertion tool 102 may include one or more sensors 104, which records the patient telemetry data, including real-time, simultaneous Pa, Pd, and electrocardiographic waveforms. The one or more sensors 104 may include a first sensor 104A and a second sensor 104B.

Figure 3B:
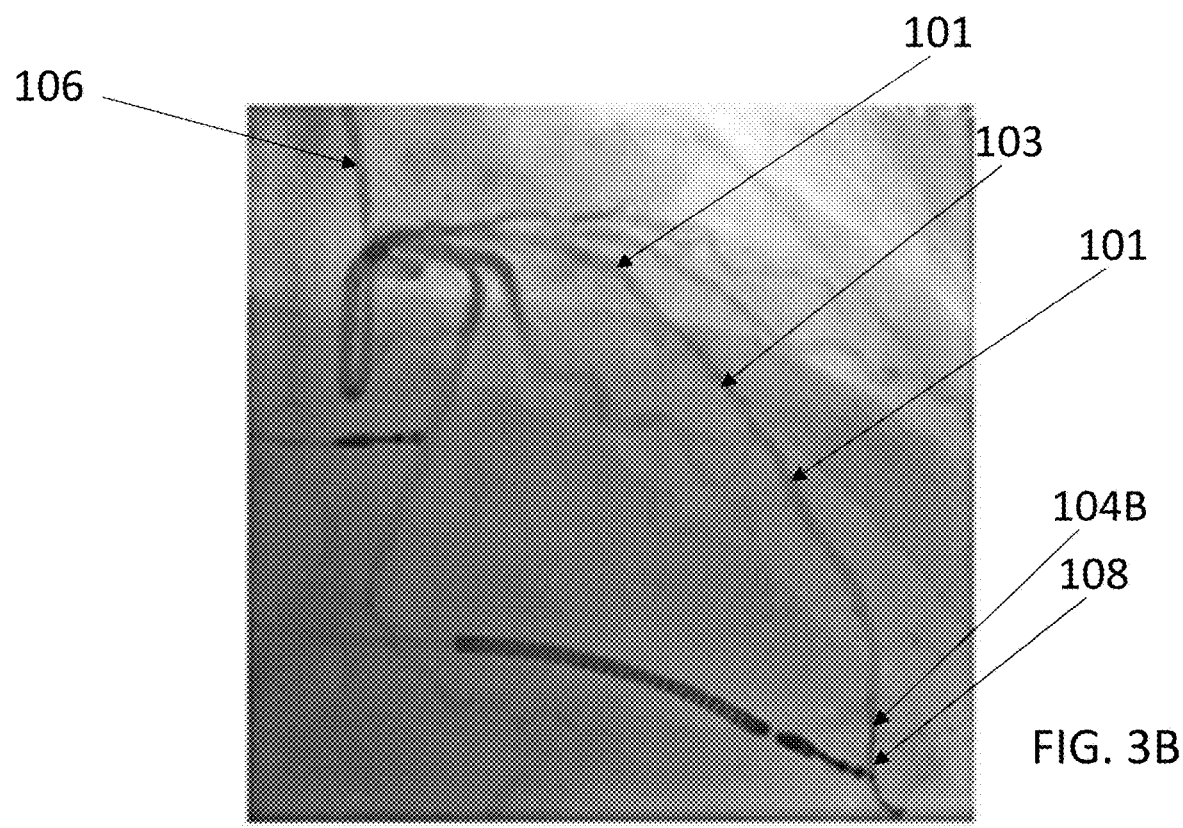
FIG. 3B depicts an example angiogram showing the example system of FIG. 3A, consistent with implementations of the current subject matter.

In some implementations, the first sensor 104A may be positioned within the aorta and/or at the coronary artery ostium. The first sensor 104A may be located on and/or integrated with at least a portion of the catheter 106 (e.g., at an end of the catheter 106) and/or on at least a portion of the pressure wire 108, such as a portion upstream of a coronary artery stenosis 103 (e.g., a restriction or blockage in the blood flow path within the artery 101). The first sensor 104A may record the Pa. The second sensor 104B may be positioned beyond or downstream of the coronary artery stenosis 103 and/or may be advanced into the distal coronary artery segment. For example, the second sensor 104B may be located on and/or integrated with at least a portion of the catheter 106 and/or the pressure wire 108, such as a portion positioned downstream of the coronary artery stenosis 103. The user interface 145 and/or the display 154 may receive an instruction to guide the catheter 106 and/or the pressure wire 108 and the hemodynamic controller 110 may cause the catheter 106 and/or the pressure wire 108 to be advanced into the distal coronary artery. In some implementations, the second sensor 104B records the Pd, such as at the position within the artery 101 beyond the stenosis 103. The first and second sensors 104A, 104B may record the Pa and Pd (and waveforms related to each of the Pa and Pd) simultaneously. FIG. 3B illustrates an example angiogram showing the catheter 106 engaging a left coronary artery and a pressure wire 108 positioned in the distal segment of a left anterior descending artery 101.

Figure 4A:
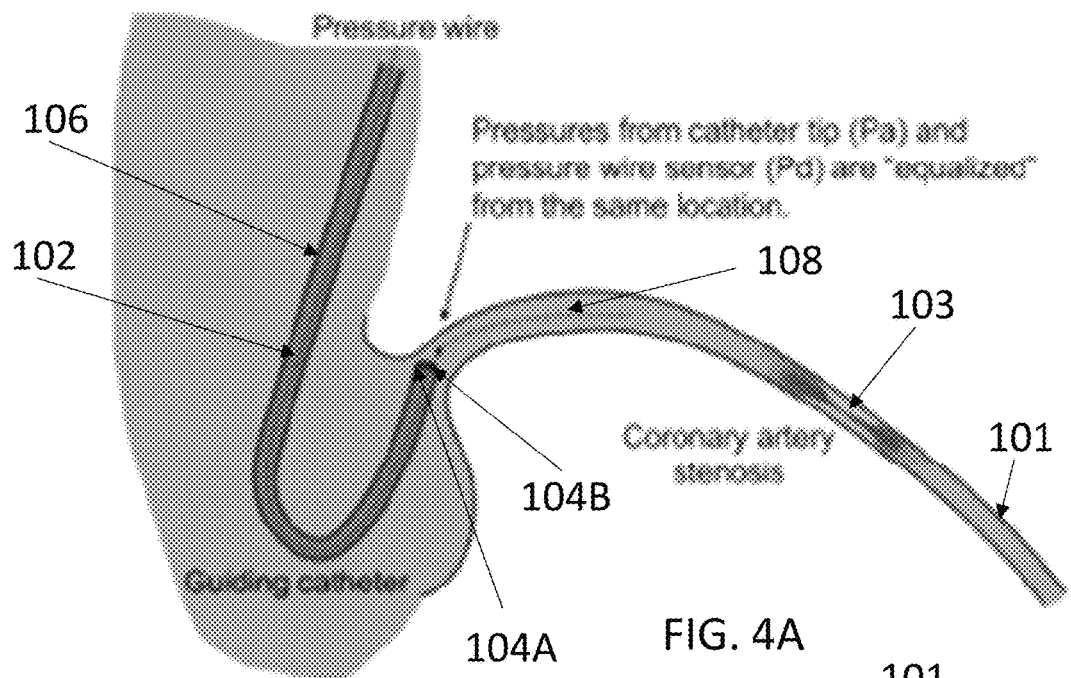
FIG. 4A depicts an example system for collection of hemodynamic measurements, consistent with implementations of the current subject matter.

FIG. 4A illustrates another example of the hemodynamic analysis system 100 in use, consistent with implementations of the current subject matter. For example, as shown in FIG. 4A, the insertion tool 102 may include a catheter 106 (e.g., a fluid-filled guiding catheter) and a pressure wire 108 extending through the catheter 106 along a blood flow path in an artery 101. The insertion tool 102 may include one or more sensors 104, which records the patient telemetry data, including real-time, simultaneous Pa, Pd, and electrocardiographic waveforms.

The one or more sensors 104 may include a first sensor 104A and a second sensor 104B. As shown in FIG. 4A, the first and second sensors 104A, 104B may be positioned at the same location. For example, the first sensor 104A, which records the Pa, may be positioned within the aorta and/or at the coronary artery ostium. The first sensor 104A may be located on and/or integrated with at least a portion of the catheter 106 and/or the pressure wire 108, such as at an end of the catheter 106 and/or pressure wire 108. The second sensor 104B may also be located on and/or integrated with at least a portion of the catheter 106 and/or the pressure wire 108, such as at an end of the catheter 106 and/or pressure wire 108, and may be positioned within the aorta and/or at the coronary artery ostium. Thus, the hemodynamic analysis system 100 shown in FIG. 4A baseline matches the Pa and Pd measurements by measuring and/or comparing the Pa and Pd at the same sampling location. This provides for more efficient, accurate, and consistent equalization or normalization of the measurements and/or calculations of the ratio of Pa to Pd, and/or a ratio of an average Pa to an average Pd.

Figure 4B:
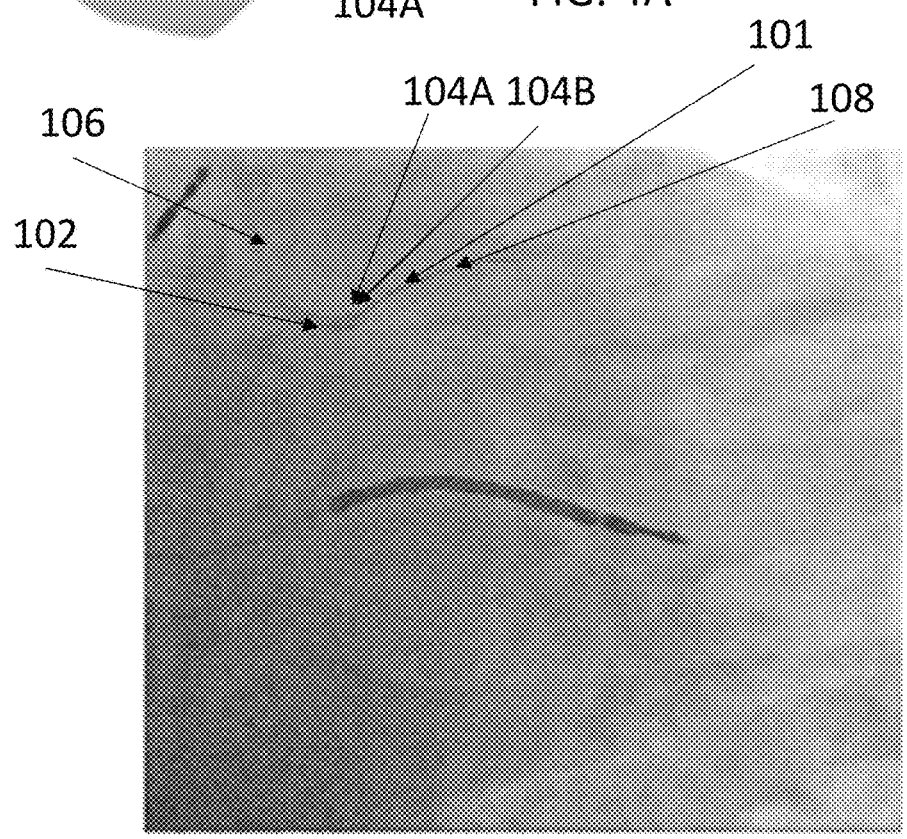
FIG. 4B depicts an example angiogram showing the example system of FIG. 4A, consistent with implementations of the current subject matter.
Figure 5:
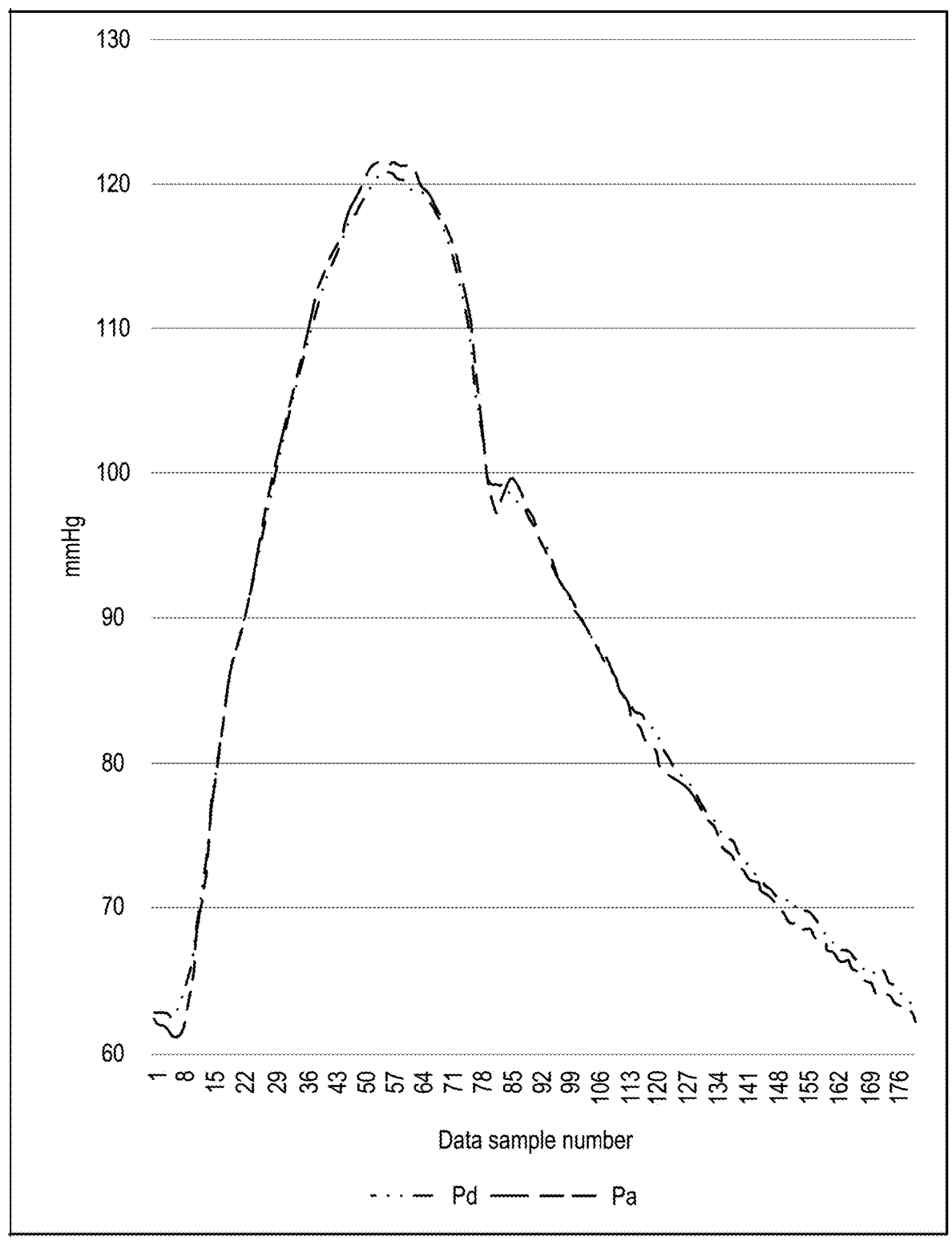
FIG. 5 depicts a graph illustrating pressure measurements across a heartbeat, consistent with implementations of the current subject matter.

While FFR measurements may generally be determined by calculating a ratio of Pa to Pd at non-specific sections of the cardiac cycle and correcting a waveform produced by the Pa to match a waveform produced by the Pd (or vice versa), the hemodynamic controller 110 consistent with implementations of the current subject matter more accurately and consistently equalizes the Pa and Pd measurements by correcting the corresponding waveforms generated at a single sampling location (e.g., when the first sensor 104A and the second sensor 104B are positioned at the same location along the blood flow path). This helps to provide a more accurate baseline waveform for the Pa and Pd measurements and for later comparison of the Pa to the Pd. FIG. 4B illustrates an example angiogram showing the catheter 106 engaging a left coronary artery and a pressure wire 108 positioned at the tip of the catheter 106 such that the first sensor 104A on the catheter is aligned with and/or positioned within a reduced range of the second sensor 104B. This configuration helps to more accurately equalize the pressure measurements recorded by the first sensor 104A and/or the second sensor 104B. FIG. 5 graphically illustrates an example of simultaneous Pa and Pd measurements during one heartbeat when the Pa and Pd measurements have been equalized.

Figure 6:
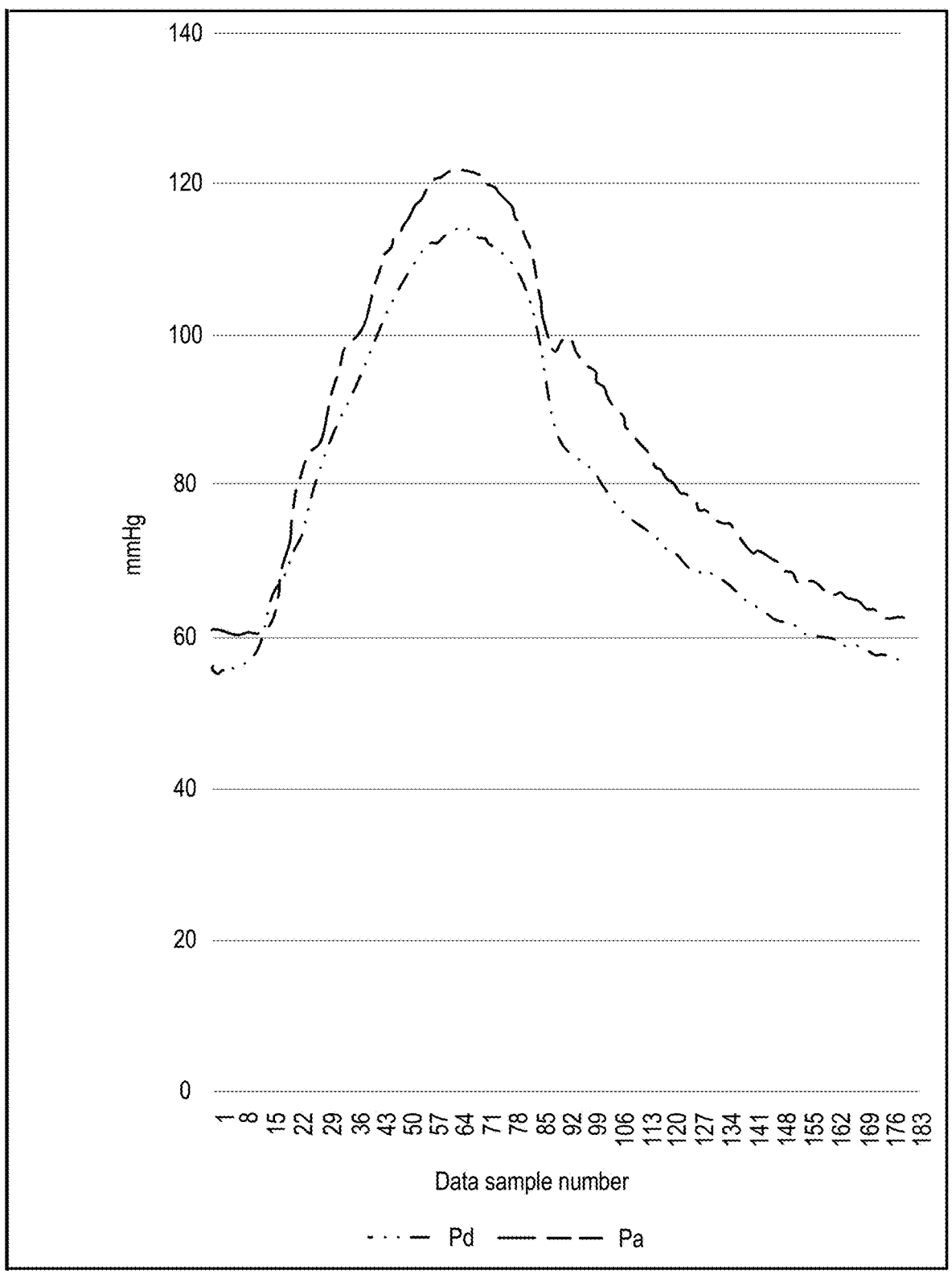
FIG. 6 depicts a graph illustrating pressure measurements across a heartbeat, consistent with implementations of the current subject matter.

After the Pa and Pd measurements are equalized at a single sampling location, at least a portion of the insertion tool 102, such as the pressure wire (and/or catheter) 108 may be advanced into a distal part of the coronary artery anatomy (e.g., see FIGS. 3A-3B). FIG. 5 graphically illustrates a comparison between Pa and Pd measurements across a heartbeat after the pressure wire 108 has been advanced beyond the stenosis, consistent with implementations of the current subject matter. Similar to the previous examples, the first sensor 104A records the Pa and the second sensor 104B records the Pd. FIG. 6 shows that the Pd measurement has been reduced across a heartbeat compared to the reference Pa measurements in the presence of anatomical resistance, such as CAD or another hemodynamic disorder, between the two pressure locations.

In some implementations, before, during, and/or after the Pa and Pd measurements are equalized and after the second sensor 104B has been advanced beyond the anatomical structure causing the resistance, the user interface of the client 140 and/or the patient monitor 152 may receive an instruction (such as from a user) to begin recording the telemetry data, including both baseline and hyperemic coronary blood flow measurements (e.g. pressures, temperatures, blood velocities, and the like). For example, based on the instructions, the hemodynamic controller 110 may cause the baseline measurements to be recorded by the first and/or second sensors 104A, 104B before a medication, such as adenosine, is introduced to the patient's coronary system, such as through the channel in the guiding catheter 106. In some implementations, the hemodynamic controller 110 causes the hyperemic coronary blood flow measurements to be recorded by the first and/or second sensors 104A, 104B after the medication is introduced to the patient's coronary system. The medication causes the vessels and/or arteries to dilate, thus increasing blood flow, and providing more usable pressure measurements.

Based on the recorded baseline and hyperemic coronary blood flow measurements for each heartbeat, the hemodynamic controller 110 may determine and/or identify a diastolic, non-diastolic, and/or whole-cycle complement of a ratio of the Pd to the Pa. In other words, the hemodynamic controller 110 may determine and/or identify a diastolic, non-diastolic, and/or whole-cycle 1-Pd/Pa for each heartbeat. The controller may aggregate (e.g., average) the diastolic, non-diastolic, and/or whole-cycle complement of the ratio of the Pd to the Pa. The aggregated complement of the ratio of the Pd to the Pa may include the mean, median, moving average, maximum, minimum, and/or other parameter, such as across a single heartbeat and/or a plurality of heartbeats.

In some implementations, the minimum complement of the ratio of the Pd to the Pa (e.g., the minimum 1-Pd/Pa measurement) is determined and/or identified by the hemodynamic controller 110 during baseline coronary flow, such as when microvascular resistance is the greatest, and the maximum complement of the ratio of the Pd to the Pa (e.g., the maximum 1-Pd/Pa measurement) is determined and/or identified by the hemodynamic controller 110 during hyperemia, when microvascular resistance is minimal due to the medication-induced dilation of the vessels. In some implementations, the minimum complement of the ratio of the Pd to the Pa and/or the maximum complement of the ratio of the Pd to the Pa may be identified and/or determined from a sample of aggregated complements of the ratio of the Pd to the Pa determined across a sample of a predetermined number of heartbeats, and/or the number of heartbeats between medication injection and a return to baseline. For example, the sample of heartbeats may include 1 to 5 heartbeats, 5 to 10 heartbeats, 10 to 15 heartbeats, 15 to 20 heartbeats, 20 to 25 heartbeats, 25 to 30 heartbeats, 30 to 35 heartbeats, 35 to 40 heartbeats, 40 to 45 heartbeats, 45 to 50 heartbeats, 50 to 55 heartbeats, 55 to 60 heartbeats, 60 to 65 heartbeats, 65 to 70 heartbeats, 70 to 75 heartbeats, 75 to 80 heartbeats, 80 to 85 heartbeats, 85 to 90 heartbeats, 90 to 95 heartbeats, or greater, and/or other ranges there between. In some implementations, the minimum complement of the ratio of the Pd to the Pa and/or the maximum complement of the ratio of the Pd to the Pa may be identified and/or determined from a sample of aggregated complements of the ratio of the Pd to the Pa determined across a period of time, such as approximately 1 to 10 seconds, 10 to 30 seconds, 30 to 60 seconds, or greater.

Figure 7:
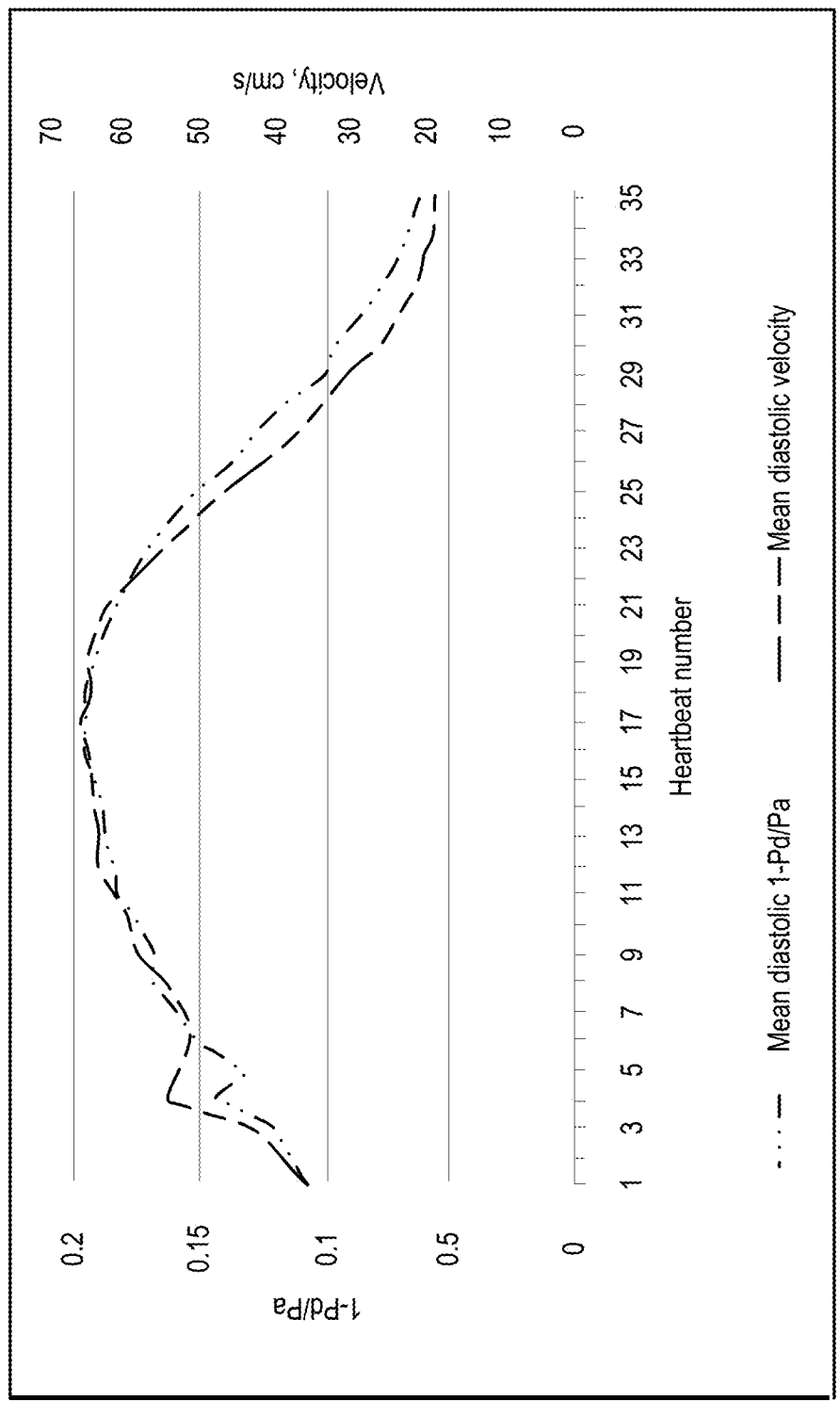
FIG. 7 depicts a graph illustrating a comparison between a mean diastolic pressure measurement and a mean diastolic velocity measurement, consistent with implementations of the current subject matter.

FIG. 7 graphically illustrates a beat-by-beat comparison of a mean diastolic complement of the ratio of the Pd to the Pa with a mean diastolic blood velocity following an intracoronary bolus of adenosine to induce hyperemia. Maximum values of each of the mean complement of the ratio of the Pd to the Pa and blood velocity occurs at hyperemia, while minimum values of each of the mean complement of the ratio of the Pd to the Pa and blood velocity occurs when the coronary flow returns to baseline. In this example, measurements were taken over a heartbeat sample of 35 heartbeats. As shown in the graphical representation in FIG. 7, using the complement of the ratio of the Pd to the Pa provides more accurate and consistent data for hemodynamic disorder detection, while minimizing artifacts, compared to relying on blood velocities to detect whether a hemodynamic disorder exists, particularly in the diastolic period between the maximum complement of the ratio of the Pd to the Pa and the baseline complement of the ratio of the Pd to the Pa.

Determining the complement of the ratio of the Pd to the Pa may desirably take into account telemetry data measured across the entire coronary vasculature including both the microvasculature and larger epicardial vessels. This combines the benefits of both CFR and FFR measurements and minimizes the inconsistencies and inaccuracies of each measurement individually. For example, the complement of the ratio of the Pd to the Pa (e.g., 1-Pd/Pa) represents the proportion of resistance caused by an anatomic restriction (e.g., epicardial vessel anatomy) positioned between the two pressure sensors (e.g., the first and second pressure sensors 104A, 104B), compared to total coronary artery resistance of the entire interrogated vessel (e.g., the entire epicardial vessel plus distal microvasculature).

Figure 8A:
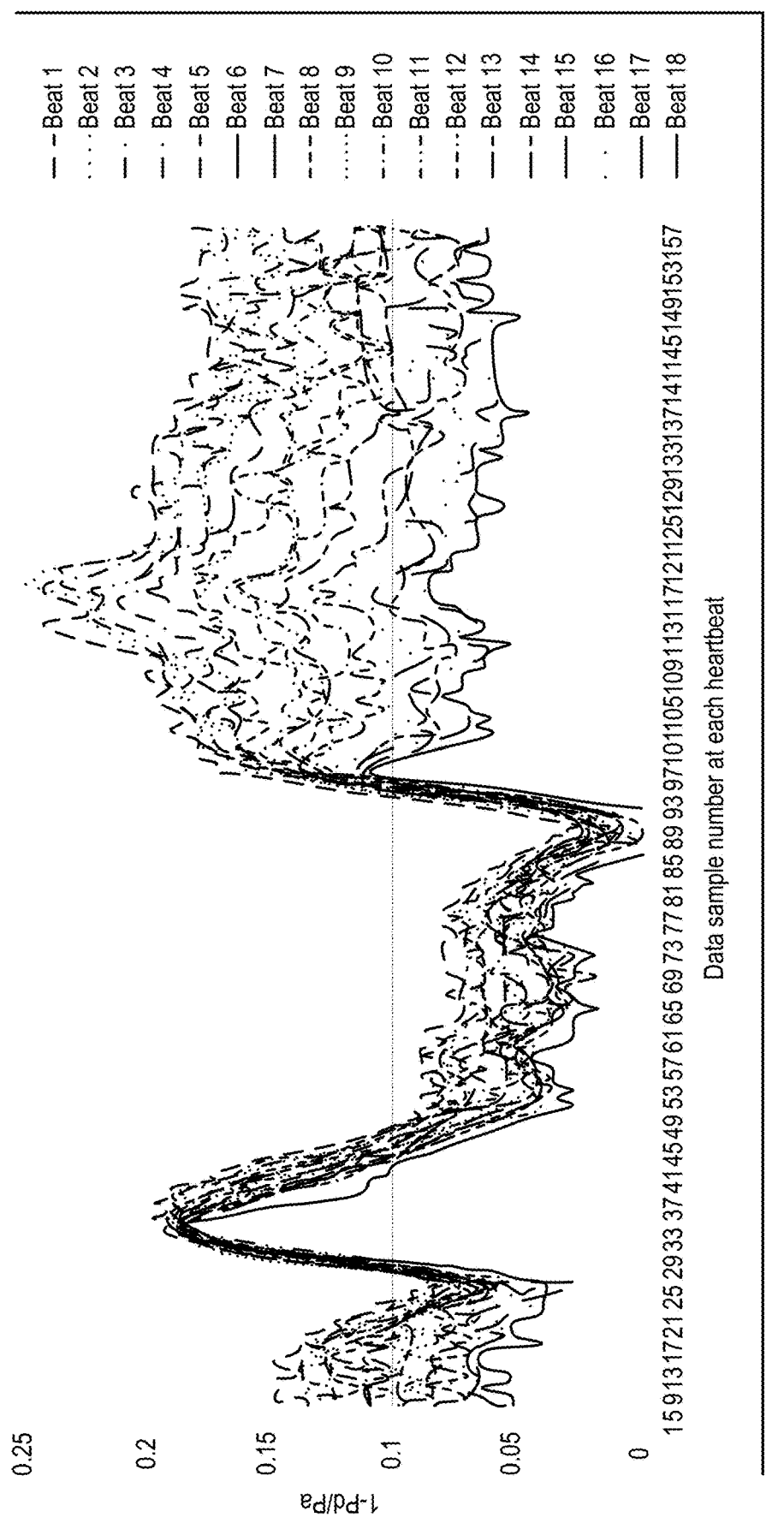
FIGS. 8A and 8B graphically depict a beat-by-beat comparison of diastolic pressure-derived coronary flow reserve and a Doppler-derived blood velocity, consistent with implementations of the current subject matter.
Figure 8B:
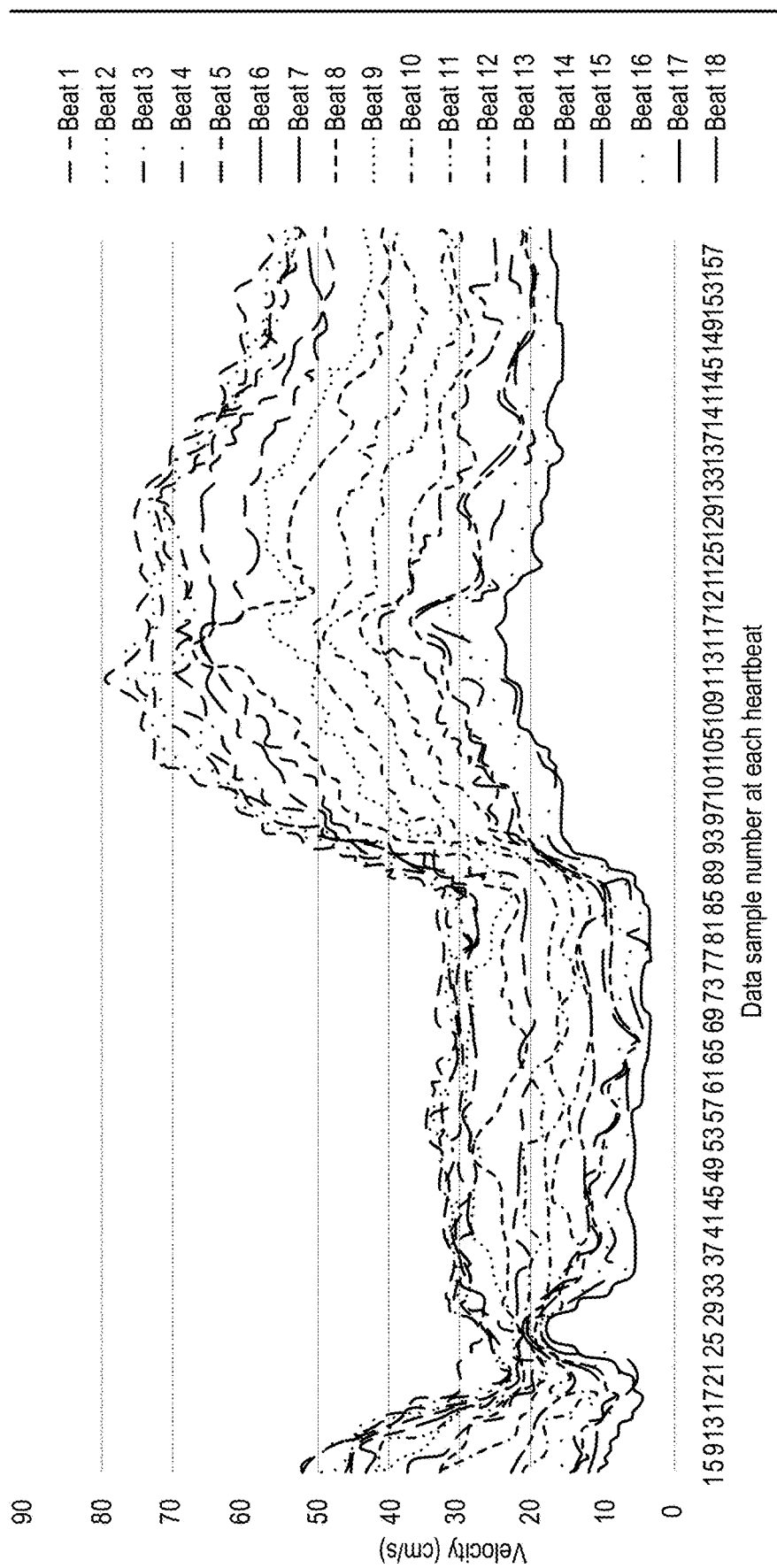

FIGS. 8A and 8B further illustrate the improved accuracy of measurements and hemodynamic disorder detection using the complement of the ratio of the Pd to the Pa (e.g., 1-Pd/Pa). For example, FIGS. 8A and 8B illustrate a beat-by-beat comparison between pressure-derived complement of the ratio of the Pd to the Pa (FIG. 8A) and Doppler-derived blood velocity (FIG. 8B) following adenosine-induced hyperemia and a return to baseline coronary flow. As shown in FIG. 8A, the pressure-derived complement of the ratio of the Pd to the Pa provides more accurate measurements through the length of each heartbeat, as determination of the complement of the ratio of the Pd to the Pa takes into account telemetry data measured across the entire coronary vasculature. For example, while there are some similarities in the diastolic period of each heartbeat in each measurement (e.g., between data sample 100 to the end), there are significant differences between the complement of the ratio of the Pd to the Pa and the blood velocities determined in the systolic period (e.g., between data sample 1 to 100), particularly at the peaks and troughs during this period. The complement of the ratio of the Pd to the Pa provides an improved indicator by including aggregated data during the diastolic period and excluding data recorded during the systolic period. Additionally, and/or alternatively, the complement of the ratio of the Pd to the Pa may provide an improved indicator by including aggregated data across the entire cardiac cycle, including both the systolic period and the diastolic period. This may reduce the differences in the data recorded during the systolic period by averaging the peaks and troughs, and may provide a better indicator of the overall health of the cardio vasculature.

In some implementations, based on the identified and/or determined maximum and minimum complements of the ratio of the Pd to the Pa, the hemodynamic controller 110 may determine the diastolic, non-diastolic, and/or whole cycle pressure-derived CFR (CFRp). To calculate the CFRp, the hemodynamic controller 110 may determine a ratio of the maximum complement of the ratio of the Pd to the Pa to the minimum complement of the ratio of the Pd to the Pa. The ratio of the maximum complement of the ratio of the Pd to the Pa to the minimum complement of the ratio of the Pd to the Pa further improves the accuracy and ability to detect a hemodynamic disorder. For example, a ratio of the maximum complement of the ratio of the Pd to the Pa to the complement of the ratio of the Pd to the Pa generally yields values greater than or equal to 1.0. In some implementations, a ratio of the maximum complement of the ratio of the Pd to the Pa to the minimum complement of the ratio of the Pd to the Pa that is less than or equal to 2.0 demonstrates abnormal CFRp and indicates that the patient is at a greater risk of adverse cardiac events, such as a hemodynamic disorder. In some implementations, the ratio of the maximum complement of the ratio of the Pd to the Pa to the minimum complement of the ratio of the Pd to the Pa that is less than or equal to 1.0, 3.0 to 4.0, 4.0 to 5.0, 5.0 to 6.0, 6.0 to 7.0, 7.0 to 8.0 or lower demonstrates abnormal CFRp and indicates that the patient is at a greater risk of adverse cardiac events, such as a hemodynamic disorder. To further illustrate the ratio of the maximum complement of the ratio of the Pd to the Pa to the minimum complement of the ratio of the Pd to the Pa, the hemodynamic controller 110 may use the following equation to determine the CFRp:

$$CFRp = \frac{1 - \left(\frac{Pd}{Pa}\right)_{maximum}}{1 - \left(\frac{Pd}{Pa}\right)_{minimum}} \qquad \text{Equation (1)}$$

where Pd is the distal coronary pressure, Pa is the arterial pressure, 1-Pd/Pa is the complement of the ratio of the Pd to the Pa, the maximum complement of the ratio of the Pd to the Pa is identified and/or determined during hyperemia at diastole and/or across an entire cardiac cycle (including both systole and diastole), and the minimum complement of the ratio of the Pd to the Pa is identified and/or determined during the return to baseline at diastole. In some implementations, Equation (1) may be simplified as follows:

$$CFRp = \frac{\left(\frac{Pa-Pd}{Pa}\right)_{maximum}}{\left(\frac{Pa-Pd}{Pa}\right)_{minimum}} \qquad \text{Equation (2)}$$

where Pd is the distal coronary pressure and Pa is the arterial pressure. The CFRp may be determined and displayed, via the user interface of the patient monitor 152 (e.g., the display 154) and/or the user interface 145 of the client 140.

Figure 9:
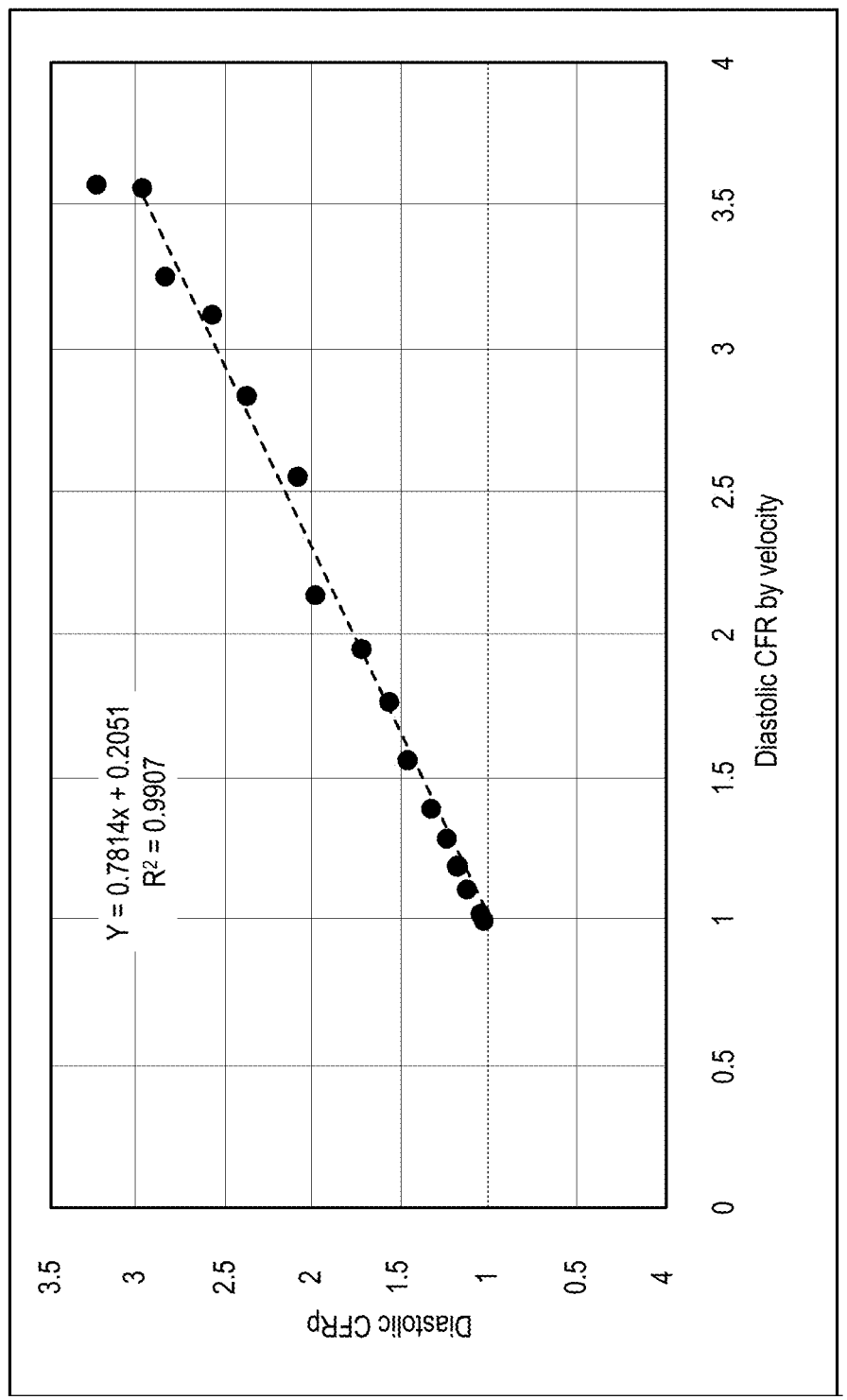
FIG. 9 depicts a graph illustrating a beat-by-beat comparison of diastolic pressure-derived coronary flow reserve and a CFR-based coronary flow reserve, consistent with implementations of the current subject matter.

The CFRp represents a ratio of instantaneous pressure gradients across the interrogated coronary artery segment determined at maximal and resting coronary flow states, each of which is respectively standardized by Pa pressure at the time of the gradient measurement. The system described herein may provide a single insertion tool to simultaneously quantify disease affecting both large-caliber coronary arteries and its distal microvasculature. As described herein, this desirably more accurately detects the existence of a hemodynamic disorder and/or the likelihood that an adverse cardiac event may occur. Additionally and/or alternatively, the hemodynamic controller 110 may determine the maximum and minimum complements of the ratio of the Pd to the Pa during the diastolic period, non-diastolic period, and/or whole-cycle of each heartbeat to minimize artifacts and variance in the measurements. Furthermore, measurements may be repeated across multiple heartbeats to identify and/or determine the complement of the ratio of the Pd to the Pa values during both baseline flow and hyperemia. Thus, this approach further improves the ability to more accurately detect hemodynamic disorders. As an example, FIG. 9 shows a correlation between CFRp and CFR measurements, but the data (e.g., diastolic pressure measurements) underlying the determined CFRp, consistent with implementations of the current subject matter, more accurately, quickly, and consistently detects hemodynamic disorders, while generating more reproducible results. Accordingly, the system described herein can identify individuals with significant microvascular disease who may otherwise have "normal" FFR and/or CFR results that delay the appropriate therapy and conceal risk of adverse clinical outcomes.

Figure 10:
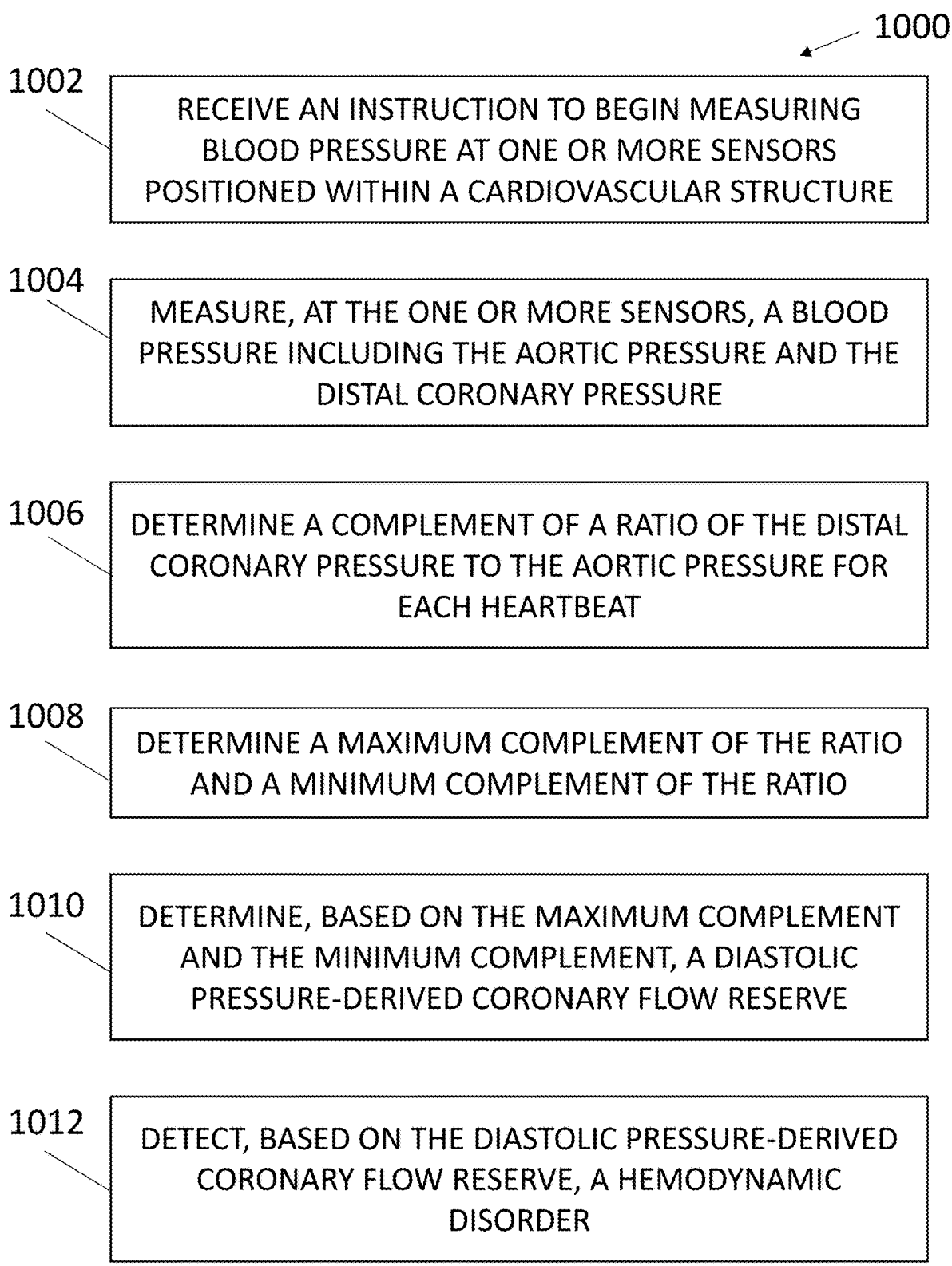
FIG. 10 depicts a flowchart illustrating a process for detecting a hemodynamic disorder, in accordance with some example embodiments.

FIG. 10 depicts a flowchart illustrating a process 1000 for detecting hemodynamic disorders, in accordance with some example embodiments. Referring to FIGS. 1-9, the process 1000 may be performed by the hemodynamic analysis system 100.

At 1002, a controller (e.g., the hemodynamic controller 110) may receive an instruction, such as via a user interface, to begin measuring a blood pressure at one or more sensors (e.g., the one or more sensors 104, including the first and second sensors 104A, 104B). As described herein, the one or more sensors may be coupled to an insertion tool that is at least partially inserted into the patient, such as into a blood vessel and/or artery of the patient. For example, the user interface may receive a user input indicating one or more aspects of a measurement protocol, such as a sampling rate, a sampling interval, a start time, an end time, and/or the like.

Based on the received instruction, at 1004, the controller may cause the one or more sensors to measure the blood pressure. In some implementations, a first sensor measures an aortic pressure (Pa) and a second sensor measures a distal coronary pressure (Pd). The first sensor may be located on a first insertion tool, and the second sensor may be located on a second insertion tool passing through the first insertion tool. In other implementations, the first sensor and the second sensor may both be located on the first insertion tool and/or the second insertion tool passing through the first insertion tool.

In some implementations, the aortic pressure and distal coronary pressures may be equalized and/or otherwise calibrated at a single location. In some implementations, after the aortic pressure and the distal coronary pressures are equalized, the second sensor recording the distal coronary pressure may be advanced further into the patient's artery or vessel, such as beyond a possible anatomical restriction in the artery or vessel.

Additionally and/or alternatively, a medication, such as adenosine may be introduced to the patient's blood flow through the artery or vessel via the insertion tool. The medication may cause the patient's artery or vessel to dilate, thereby causing an increase in blood flow through the artery or vessel. The one or more sensors may record the respective pressures before, during, and/or after the medication has been introduced to the patient, at one or more sampling rates, to capture the pressure before, during, and/or after the medication has been introduced. In some implementations, the controller stops recording the pressures at the one or more sensors when the controller detects that a baseline pressure has been reached. In some implementations, the controller stops recording the pressures at the one or more sensors according to an instruction received via the user interface, according to a predetermined time interval, after a predetermined number of heartbeats, and/or the like.

At 1006, based on the pressure measurements, the controller may determine a complement of a ratio of the distal coronary pressure to the aortic pressure (e.g., 1-Pd/Pa) for each heartbeat. The complement of the ratio of the distal coronary pressure to the aortic pressure may additionally and/or alternatively be aggregated (e.g., averaged) across one or more heartbeats.

At 1008, the controller may, based on the aggregated ratios, determine a maximum complement of the ratio of the distal coronary pressure to the aortic pressure (e.g., a maximum 1-Pd/Pa) and a minimum complement of the ratio of the distal coronary pressure to the aortic pressure (e.g., a minimum 1-Pd/Pa). The maximum complement may occur during the hyperemic period, such as after the medication has been introduced to the patient. The minimum complement may occur during and/or at the return to the baseline. The maximum and minimum complements may be determined during the diastolic (and/or non-diastolic, or whole-cycle) period of the heartbeat to further improve the accuracy of the measurements and improve the ability to more quickly detect hemodynamic disorders.

At 1010, the controller may, based on the maximum complement and minimum complement, determine a pressure-derived coronary flow reserve (e.g., CFRp). The pressure-derived coronary flow reserve may include a ratio of the maximum complement to the minimum complement (e.g., see Equations (1) and (2)). In some implementations, the pressure-derived coronary flow reserve (and/or one or more measured and/or calculated parameters, such as the pressures, complements, ratios, and/or the like) may be transmitted to a display (such as the display 154 and/or the user interface 145) and presented via the display in a numerical and/or graphical representation.

At 1012, the controller may detect, based on the pressure-derived coronary flow reserve, a hemodynamic disorder. For example, the controller may compare the pressure-derived coronary flow reserve to an initial threshold. Values less than the initial threshold may indicate that the patient is likely to develop an adverse cardiac event. Values greater than or equal to the secondary threshold may indicate a hemodynamic disorder, such as an anatomical restriction. The secondary threshold may be greater than or equal to the initial threshold. For example, the initial threshold may be approximately 2.0. The secondary threshold may be 5.0 to 6.0, 6.0 to 7.0, 7.0 to 8.0 or greater. In some implementations, based on the detection of the hemodynamic disorder, the controller may generate an alert, such as via the display. In some implementations, the controller described herein may receive one or more measurements and detect, based on the measurements, the CFRp, an FFR, a resting Pd/Pa, and/or the like, a hemodynamic disorder within the cardiovascular structure of the patient. For example, as described herein, the controller may compare the CFRp, the FFR, and/or the resting Pd/Pa to a threshold and detect the hemodynamic disorder when the CFRp, the FFR, and/or the resting Pd/Pa are less than or equal to the threshold, and/or greater than or equal to the threshold as described herein. In some implementations, during and/or after the measurements are recorded, the one or more measurements and/or determined parameters may be transmitted from the one or more sensors to the client and/or the patient monitor and/or be displayed at the client and/or the patient monitor.

Figure 11:
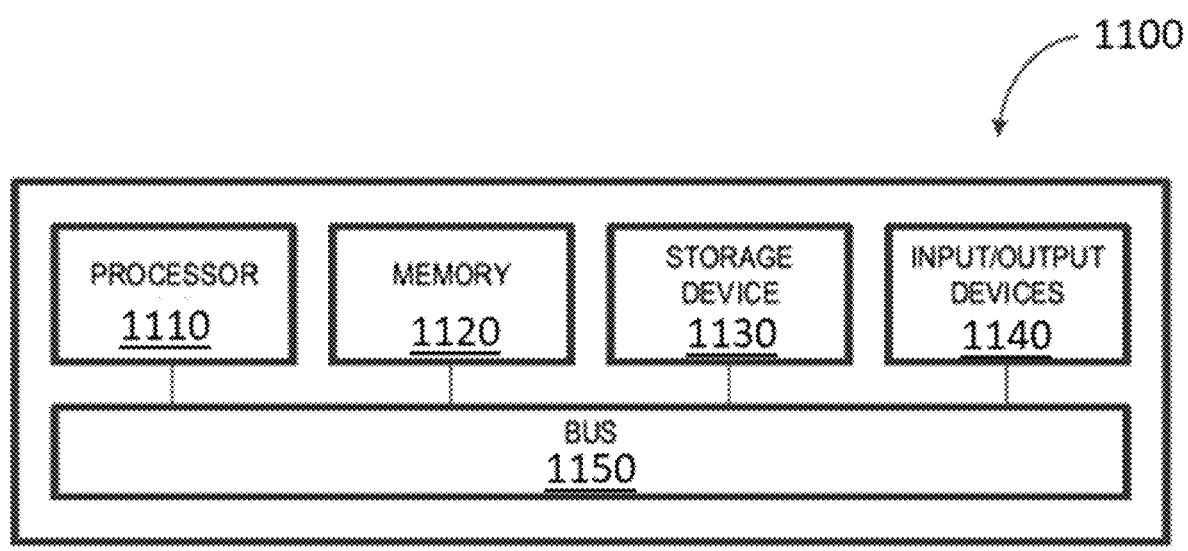
FIG. 11 depicts a block diagram illustrating a computing system, in accordance with some example embodiments.

FIG. 11 depicts a block diagram illustrating a computing system 1100 consistent with implementations of the current subject matter. Referring to FIGS. 1 and 11, the computing system 1100 can be used to implement the hemodynamic analysis system 100, and/or any components therein.

As shown in FIG. 11, the computing system 1100 can include a processor 1110, a memory 1120, a storage device 1130, and input/output devices 1140. The processor 1110, the memory 1120, the storage device 1130, and the input/output devices 1140 can be interconnected via a system bus 1150. The processor 1110 is capable of processing instructions for execution within the computing system 1100. Such executed instructions can implement one or more components of, for example, the hemodynamic analysis system 100. In some example embodiments, the processor 1110 can be a single-threaded processor. Alternatively, the processor 1110 can be a multi-threaded processor. The processor 1110 is capable of processing instructions stored in the memory 1120 and/or on the storage device 1130 to present graphical information for a user interface provided via the input/output device 1140.

The memory 1120 is a computer readable medium such as volatile or non-volatile that stores information within the computing system 1100. The memory 1120 can store data structures representing configuration object databases, for example. The storage device 1130 is capable of providing persistent storage for the computing system 1100. The storage device 1130 can be a floppy disk device, a hard disk device, an optical disk device, or a tape device, or other suitable persistent storage means. The input/output device 1140 provides input/output operations for the computing system 1100. In some example embodiments, the input/output device 1140 includes a keyboard and/or pointing device. In various implementations, the input/output device 1140 includes a display unit for displaying graphical user interfaces.

According to some example embodiments, the input/output device 1140 can provide input/output operations for a network device. For example, the input/output device 1140 can include Ethernet ports or other networking ports to communicate with one or more wired and/or wireless networks (e.g., a local area network (LAN), a wide area network (WAN), the Internet).

In some example embodiments, the computing system 1100 can be used to execute various interactive computer software applications that can be used for organization, analysis and/or storage of data in various formats. Alternatively, the computing system 1100 can be used to execute software applications. These applications can be used to perform various functionalities, e.g., planning functionalities (e.g., generating, managing, editing of spreadsheet documents, word processing documents, and/or any other objects, etc.), computing functionalities, communications functionalities, etc. The applications can include various add-in functionalities or can be standalone computing products and/or functionalities. Upon activation within the applications, the functionalities can be used to generate the user interface provided via the input/output device 1140. The user interface can be generated and presented to a user by the computing system 1100 (e.g., on a computer screen monitor, etc.).

One or more aspects or features of the subject matter described herein can be realized in digital electronic circuitry, integrated circuitry, specially designed ASICs, field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example, as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including acoustic, speech, or tactile input. Other possible input devices include touch screens or other touch-sensitive devices such as single or multi-point resistive or capacitive track pads, voice recognition hardware and software, optical scanners, optical pointers, digital image capture devices and associated interpretation software, and the like.

Although the disclosure, including the figures, described herein may describe and/or exemplify different variations separately, it should be understood that all or some, or components of them, may be combined.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:
   at least one data processor; and
   at least one memory storing instructions which, when executed by the at least one data processor, result in operations comprising:
      receiving, from one or more sensors positioned within a cardiovascular structure of a patient, a blood pressure over a plurality of heartbeats, the blood pressure comprising an aortic pressure and a distal coronary pressure;
      determining a complement of a ratio of the distal coronary pressure to the aortic pressure for each heartbeat of the plurality of heartbeats;
      determining, based on the complement of the ratio, a maximum complement of the ratio and a minimum complement of the ratio; determining, based on the maximum complement and the minimum complement, a pressure-derived coronary flow reserve, the pressure-derived coronary flow reserve comprising a ratio of the maximum complement to the minimum complement
      detecting, based on the complement of the ratio of the distal coronary pressure to the aortic pressure, a hemodynamic disorder within the cardiovascular structure of the patient; and
      generating, based on the detection of the hemodynamic disorder, an alert.

2. The system of claim 1, wherein the detecting is further based on the pressure-derived coronary flow reserve.

3. The system of claim 1, wherein the determining the complement of the ratio further comprises aggregating the complement of the ratio of the plurality of heartbeats; and determining, based on the aggregated complement of the ratio, the maximum complement and the minimum complement.

4. The system of claim 2, wherein the detecting further comprises comparing the pressure-derived coronary flow reserve to a threshold; and detecting the hemodynamic disorder when the pressure-derived coronary flow reserve is less than the threshold.

5. The system of claim 1, wherein the one or more sensors comprises a first sensor coupled to a first insertion tool and a second sensor coupled to a second insertion tool, the first sensor configured to measure the aortic pressure and the second sensor configured to measure the distal coronary pressure.

6. The system of claim 5, wherein the operations further comprise: equalizing the aortic pressure and the distal coronary pressure when the first sensor and the second sensor are positioned at the same location.

7. The system of claim 5, wherein the receiving further comprises: receiving the aortic pressure from the first sensor and the distal coronary pressure from the second sensor when the second sensor is positioned downstream of an anatomical restriction.

8. The system of claim 1, wherein the receiving further comprises: receiving the aortic pressure and the distal coronary pressure after a medication has been introduced to the cardiovascular structure, the medication causing the cardiovascular structure to dilate.

9. The system of claim 1, wherein the cardiovascular structure comprises one or more of an artery and a vessel.

10. The system of claim 1, wherein the alert indicates that the pressure-derived coronary flow reserve is greater than or equal to a threshold.

11. A method, comprising:
    receiving, from one or more sensors positioned within a cardiovascular structure of a patient, a blood pressure over a plurality of heartbeats, the blood pressure comprising an aortic pressure and a distal coronary pressure;
    determining a complement of a ratio of the distal coronary pressure to the aortic pressure for each heartbeat of the plurality of heartbeats;
    determining, based on the complement of the ratio, a maximum complement of the ratio and a minimum complement of the ratio; determining, based on the maximum complement and the minimum complement, a pressure-derived coronary flow reserve, the pressure-derived coronary flow reserve comprising a ratio of the maximum complement to the minimum complement
    detecting, based on the complement of the ratio of the distal coronary pressure to the aortic pressure, a hemodynamic disorder within the cardiovascular structure of the patient; and
    generating, based on the detection of the hemodynamic disorder, an alert, wherein the alert is a notification provided via a user interface.

12. The method of claim 11, wherein the detecting is further based on the pressure-derived coronary flow reserve.

13. The method of claim 11, wherein the determining the complement of the ratio further comprises aggregating the complement of the ratio of the plurality of heartbeats; and determining, based on the aggregated complement of the ratio, the maximum complement and the minimum complement.

14. The method of claim 12, wherein the detecting further comprises comparing the pressure-derived coronary flow reserve to a threshold; and detecting the hemodynamic disorder when the pressure-derived coronary flow reserve is less than the threshold.

15. The method of claim 11, wherein the one or more sensors comprises a first sensor coupled to a first insertion tool and a second sensor coupled to a second insertion tool, the first sensor configured to measure the aortic pressure and the second sensor configured to measure the distal coronary pressure.

16. The method of claim 15, further comprising: equalizing the aortic pressure and the distal coronary pressure when the first sensor and the second sensor are positioned at the same location.

17. A non-transitory computer-readable storage medium including program code, which when executed by at least one data processor, cause operations comprising:
    receiving, from one or more sensors positioned within a cardiovascular structure of a patient, a blood pressure over a plurality of heartbeats, the blood pressure comprising an aortic pressure and a distal coronary pressure;
    determining a complement of a ratio of the distal coronary pressure to the aortic pressure for each heartbeat of the plurality of heartbeats;

determining, based on the complement of the ratio, a maximum complement of the ratio and a minimum complement of the ratio; determining, based on the maximum complement and the minimum complement, a pressure-derived coronary flow reserve, the pressure-derived coronary flow reserve comprising a ratio of the maximum complement to the minimum complement detecting, based on the complement of the ratio of the distal coronary pressure to the aortic pressure, a hemodynamic disorder within the cardiovascular structure of the patient; and generating, based on the detection of the hemodynamic disorder, an alert.

* * * * *